(12) United States Patent  
Roy et al.

(10) Patent No.: US 8,652,186 B2  
(45) Date of Patent: Feb. 18, 2014

(54) SYSTEM AND METHOD FOR SELECTING FOLLICULAR UNITS FOR HARVESTING

(75) Inventors: Robert N. Roy, Fremont, CA (US); Shehrzad A. Qureshi, Palo Alto, CA (US)

(73) Assignee: Restoration Robotics, Inc., San Jose, CA (US)

( * ) Notice: Subject to any disclaimer, the term of this patent is extended or adjusted under 35 U.S.C. 154(b) by 569 days.

(21) Appl. No.: 12/824,801

(22) Filed: Jun. 28, 2010

(65) Prior Publication Data

US 2010/0262129 A1    Oct. 14, 2010

Related U.S. Application Data

(63) Continuation-in-part of application No. 12/133,159, filed on Jun. 4, 2008.

(51) Int. Cl.  
*A61N 5/06* (2006.01)

(52) U.S. Cl.  
USPC ................................. 607/88; 606/2

(58) Field of Classification Search  
USPC ............... 606/2–19; 607/88–94; 128/898  
See application file for complete search history.

(56) References Cited

U.S. PATENT DOCUMENTS

| | | | |
|---|---|---|---|
| 4,063,822 A | 12/1977 | deJong et al. | |
| 4,807,163 A | 2/1989 | Gibbons | |
| 5,865,744 A | 2/1999 | Lemelson | |
| 6,470,236 B2 | 10/2002 | Ohtsuki | |
| 6,477,394 B2 | 11/2002 | Rice et al. | |
| 6,504,603 B1 | 1/2003 | Schouenborg | |
| 6,547,782 B1 | 4/2003 | Taylor | |
| 6,572,625 B1 | 6/2003 | Rassman | |
| 6,585,746 B2 | 7/2003 | Gildenberg | |
| 6,949,115 B2 | 9/2005 | Mascio | |
| 7,014,336 B1 | 3/2006 | Ducharme et al. | |
| 7,130,717 B2 | 10/2006 | Gildenberg | |
| 7,206,627 B2 | 4/2007 | Abovitz et al. | |
| 7,239,909 B2 | 7/2007 | Zeman | |
| 7,290,896 B2 | 11/2007 | Dallas et al. | |
| 7,477,782 B2 | 1/2009 | Qureshi et al. | |

(Continued)

FOREIGN PATENT DOCUMENTS

| | | |
|---|---|---|
| CN | 101128156 | 2/2008 |
| WO | 00/64379 | 11/2000 |

(Continued)

OTHER PUBLICATIONS

PCT Notification of Transmittal of the International Search Report and the Written Opinion of the International Searching Authority. International Application No. PCT/US2009/045500. Forms PCT/ISA/220, 210 & 237. (15 Pages).

Mohammed Alhaddab, MD; Thomas Kohn, MD; and Mark Sidloi, BSc, Effect of Graft Size, Angle, and Intergraft Distance on Dense Packing in Hair Transplant. Dermatol Surg 2005; 31:pp. 650-654. Published by BC Decker Inc.

(Continued)

*Primary Examiner* — Aaron Roane  
(74) *Attorney, Agent, or Firm* — Lena I. Vinitskaya; Sharon Upham

(57) ABSTRACT

A system and method is provided for improving the visibility of hair on the skin surface, in a region that is bloodied or bruised, and potentially expanding the candidate pool of the hair grafts to be selected for harvesting. The system uses a light source comprising at least two emitters and the method comprises controlling the contrast between the image of the blood and the image of the skin surface. The method of the present invention may be implemented with various hair harvesting and transplantation systems, including manual, partially automated and fully automated systems.

25 Claims, 11 Drawing Sheets

(56) References Cited

U.S. PATENT DOCUMENTS

| | | |
|---|---|---|
| 7,517,107 B2 | 4/2009 | Dallas et al. |
| 7,545,487 B2 | 6/2009 | Kok et al. |
| RE42,381 E | 5/2011 | Gildenberg |
| 2002/0103500 A1 | 8/2002 | Gildenberg |
| 2004/0034282 A1 | 2/2004 | Quaid |
| 2004/0204700 A1 | 10/2004 | Weaver et al. |
| 2006/0089555 A1 | 4/2006 | Gummer et al. |
| 2007/0078466 A1 | 4/2007 | Bodduluri |
| 2008/0154247 A1 | 6/2008 | Dallarosa et al. |
| 2008/0216334 A1 | 9/2008 | Pak et al. |
| 2009/0237920 A1 | 9/2009 | Dallas et al. |
| 2009/0245601 A1 | 10/2009 | Cohen et al. |
| 2009/0306680 A1 | 12/2009 | Qureshi et al. |
| 2011/0082369 A1 | 4/2011 | Mohr et al. |
| 2011/0160589 A1 | 6/2011 | Fu et al. |

FOREIGN PATENT DOCUMENTS

| | | |
|---|---|---|
| WO | 2006/071728 | 7/2006 |
| WO | WO2008024954 | 2/2008 |
| WO | WO2008024955 | 2/2008 |

OTHER PUBLICATIONS

Rolf Hoffmann and Dominique Van Neste, "Recent Findings with Computerized Methods for Scalp Hair Growth Measurements". J Investig Dermatol Symp Proc 10: 285-288, 2005.

Robert M. Bernstein, MD, and William R. Rassman, MD. "The Logic of Follicular Unit Transplantation". Dermatologic Clinics, vol. 17, No. 2, Apr. 1999.

Translation of Examiner's First Office Action in connection with commonly assigned Chinese Patent Application No. 200980117701.0, Applicant: Restoration Robotics, Inc., dated Aug. 2, 2012 (6 pages).

Office Action mailed Nov. 20, 2012, in connection with commonly assigned U.S. Appl. No. 12/133,159 (10 pages).

Translation of Examiner's Office Action in connection with commonly assigned Japanese Patent Application No. 2011-512533, Applicant: Restoration Robotics, Inc., dated Sep. 18, 2012 (3 pages).

Examiner's First Report in connection with commonly assigned Korean Patent Application No. 2010-7026383, and translation thereof. Applicant: Restoration Robotics, Inc., dated May 9, 2012 (6 pages).

English Translation of Office Action mailed Nov. 27, 2012, in relation to commonly assigned Korean Patent Application No. 2010-7026383, 4 pages.

FUs to be ignored

"selection region-of-interest"

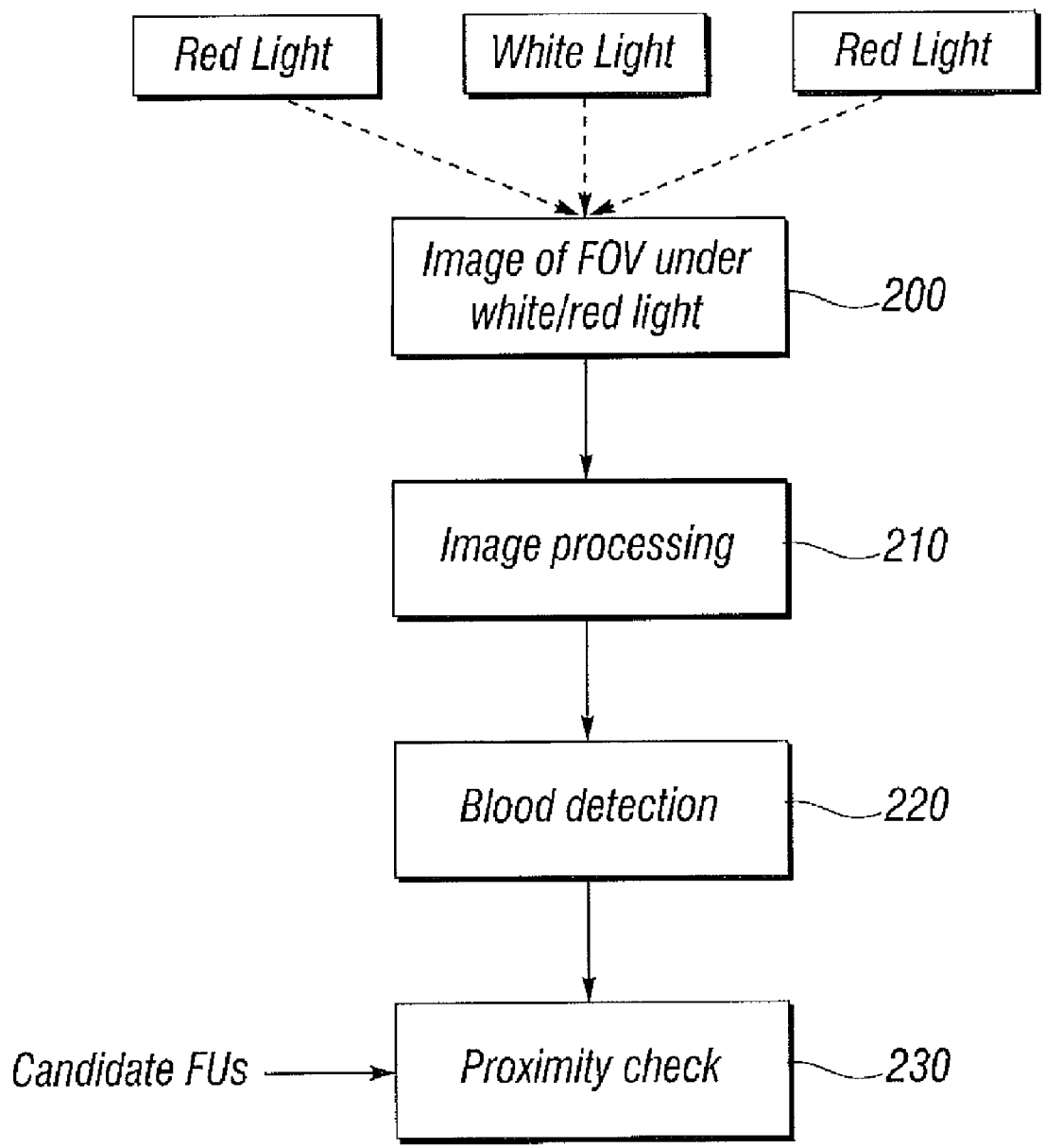

red light white light

Fig.6
Non-bloody regions of the scalp (more texture => larger variance)
Bloody regions of the scalp (less texture => lower variance)
Fig.7
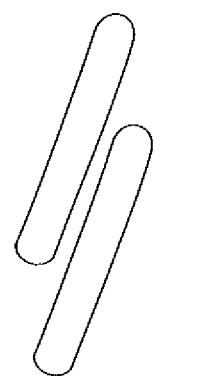
Left
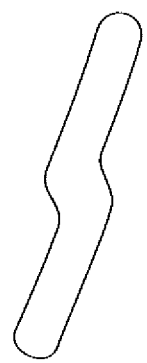
Right Policy: skip every N FU
N=1

Policy: skip every N FU
N=2

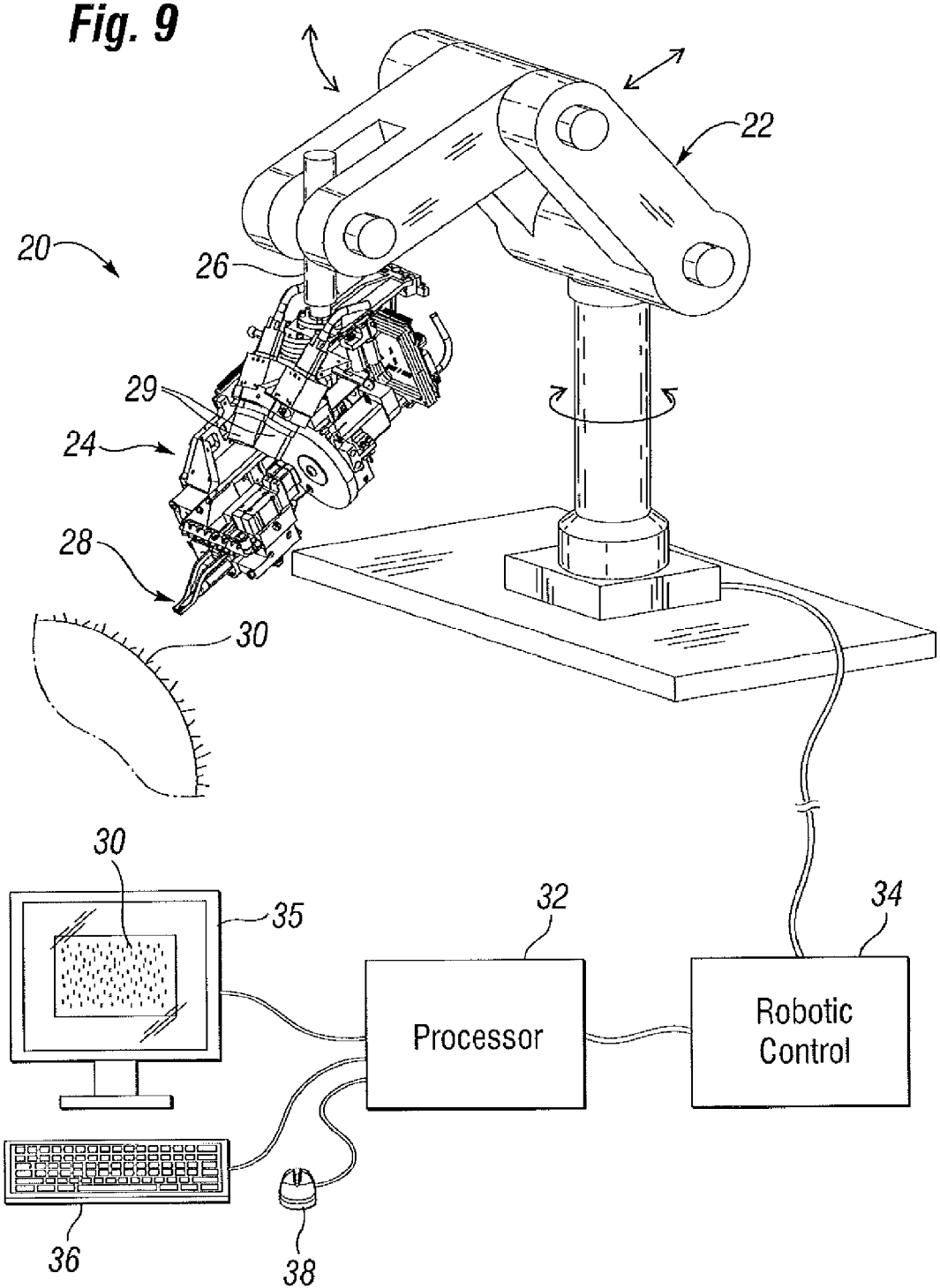

SYSTEM AND METHOD FOR SELECTING FOLLICULAR UNITS FOR HARVESTING

RELATED APPLICATIONS

This application is a continuation-in-part of the U.S. application Ser. No. 12/133,159, entitled, "System and Method for Selecting Follicular Units for Harvesting," filed Jun. 4, 2008.

FIELD OF INVENTION

The present application relates generally to hair transplantation procedures and more particularly to a system and method for selecting follicular units for hair harvesting and improving their visibility using imaging and processing techniques.

BACKGROUND

Hair transplantation procedures are well-known, and typically involve harvesting donor hair grafts from the donor areas, for example, side and back fringe areas of the patient's scalp or other surface containing hair, and implanting them in a bald area (recipient area). Historically, the harvested grafts were relatively large (3-5 mm), although more recently, the donor grafts may be single follicular units. In particular, "follicular units" (also referred to as FU or FUs) are naturally occurring aggregates of 1-3 (and much less commonly, 4-5) closely spaced hair follicles that are distributed randomly over the body surface, such as a scalp.

The follicular units may be classified, or "typed," based on the number of hairs in the unit and identified in shorthand as an "F1" for a single hair follicular unit, an "F2" for a two hair follicular unit and so on for follicular units with 3-5 hairs. It is desirable to identify follicular units based on the number of hairs in the follicular unit. For one, it is preferable to transplant certain classes of follicular units into specific regions of the scalp. For example, single hair follicular units (F1s) are commonly implanted along the hairline that frames the face. Follicular units with more than one hair (F2s, F3s, etc.) are commonly implanted in the mid-scalp and crown. This arrangement of follicular unit distribution is thought to produce a more natural appearing aesthetic result. Still, it may be desirable to utilize a variety of classes (also referred to as "types") of follicular units to provide the desired attributes for the appearance of the transplanted hair. Such attributes can include the density of hair, the direction or orientation of hair, the particular mix of types of follicular units, and/or the appearance of randomness, among other possible attributes.

Various procedures for hair transplantation have been previously disclosed, including both manual and mechanized to certain degrees of automation. In one well-known manual process, a linear portion of the scalp is removed from a donor area by dissection with a scalpel down into the fatty subcutaneous tissue. The strip is dissected (under a microscope) into the component follicular units, which are then implanted into a recipient area in respective puncture holes made by a needle. Forceps are typically used to grasp and place the follicular unit grafts into the needle puncture locations, although other instruments and methods are known for doing so. In another manual process, a hand-held punch or cannula is used to extract follicular units from a body surface one at a time for subsequent implantation in another location. This technique is known as FUE (follicular unit extraction) technique.

In utilizing any of the manual or automated systems and methods for hair transplantation, it is desirable to improve the speed and efficiency of the procedure. Regardless of the system used, certain time is often lost due to the need to select the next follicular unit to be harvested and to move the hair harvesting tool from the position of previously harvested follicular unit to the location of the next selected follicular unit. Therefore, there is a need for a system and method for automated selection mechanism for choosing follicular units for harvesting and improving efficiency of the process as a whole.

SUMMARY

In accordance with one general aspect, the present application discloses a method for improving visualization of hair for use in hair transplantation. One embodiment of such method comprises illuminating with a light source a skin surface having blood, for example, on a portion of the skin surface. The method also comprises acquiring an image of the skin surface, including the portion of the skin surface with the blood thereon. The wavelength of the light source is adjusted such that a contrast between the image of the skin surface without blood and an image of the blood is minimized and the adjusted wavelength of the light source is used to visualize or improve visualization of a hair graft located in a region of the skin surface having blood thereon.

The adjustment may comprise acquiring an image to verify that the contrast between the image of the skin without blood and the image of the blood has been minimized. If the contrast has not been minimized as desired, the step of adjusting the wavelength of the light source and acquiring an additional image(s) may be repeated until the contrast between the image of the skin without blood and the image of the blood has been minimized as desired. The method may comprise selecting the adjusted wavelength from a database.

In certain embodiments, the method may further comprise harvesting the hair graft for transplantation. In further embodiments, the method may comprise further adjusting the wavelength of the light source, for example, by restoring the original contrast to locate the blood areas again to enable visualization of a location from which the hair graft has been harvested prior to harvesting a subsequent hair graft.

According to another aspect, a system for imaging a skin surface containing hair is provided. The system may comprise a light source configured for illuminating a skin surface having blood on a portion of the skin surface, the light source comprising at least two emitters; an imaging device; and a controller configured for varying a relative contribution of each of the at least two emitters to minimize contrast between an image of the skin surface without blood and an image of the blood acquired by the imaging device, such that visibility of at least one hair follicle located in a region of the skin surface having blood thereon is improved. In certain embodiments, the light source may comprise light emitting diodes or superluminescent diodes. Also, a controller may be configured to control and to allow varying the intensity of at least one of the two emitters. The systems and methods of the present application are especially useful when implemented on, or integrated with, an automated system for hair transplantation.

Other and further embodiments, objects and advantages of the invention will become apparent from the following detailed description when read in view of the accompanying figures.

BRIEF DESCRIPTION OF THE DRAWINGS

The invention is illustrated by way of example and not limitation in the figures of the accompanying drawings, in which like references indicate similar elements, and in which:

FIG. 4 is an exemplary block diagram of the blood region detection and proximity check according to yet another filtering criterion of an embodiment of the present invention.

FIG. 6 is a print of the digital image demonstrating exemplary filtering of the candidate follicular units through blood detection using a variance filter.

FIG. 7 is a schematic representation of another exemplary filtering criterion according to an embodiment of a method of the present invention.

FIG. 9 is a depiction of an exemplary embodiment of the present invention implemented in a robotic hair harvesting procedure.

DETAILED DESCRIPTION OF THE ILLUSTRATED EMBODIMENTS

Figure 1:
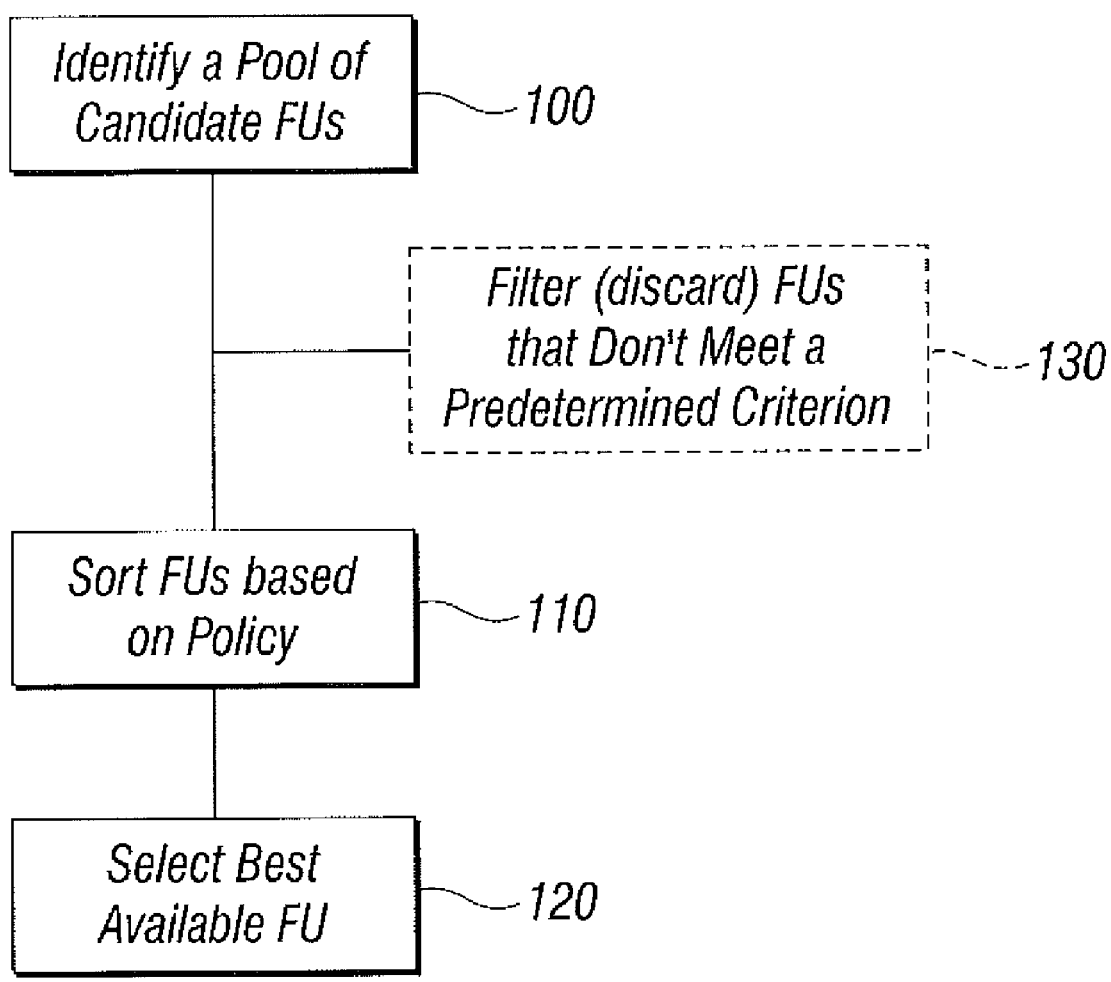
FIG. 1 is a block diagram of an example of an automatic follicular unit selection process according to an embodiment of the invention.

In the following Detailed Description, reference is made to the accompanying drawings that show by way of illustration some exemplary embodiments in which the invention may be practiced. In this regard, directional terminology, such as "top," "bottom," "distal," "proximal," etc., is used with reference to the orientation of the Figure(s) being described. Because components or embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following description, therefore, is not to be taken in a limiting sense, and the scope of the present invention is defined by the appended claims.

The adjective "automated" with reference to a system or process as a whole means that some part or all of a particular system or step in the process involves an autonomous mechanism or function; i.e., that mechanism or function does not require manual actuation. Ultimately, one or more steps in the procedure may be automated, or autonomous, with some parts requiring manual input. This definition encompasses an automated system that requires only an operator to depress an ON switch or schedule the operation, and also a system in which hand held tools are used but some mechanism of the system functions autonomously, i.e., without human input, to perform a function. Some of the automated systems described herein may also be robotically-assisted or computer/software/machine-instruction controlled. The devices and methods of the present invention are useful in manual procedures and systems, as well as in automated procedures and system, and are especially beneficial with the robotically-assisted systems and procedures. The adverb "automatically" when referring to use of a particular component of a system or a particular step in a process means that such step is accomplished autonomously, i.e., without real-time manual assistance.

The term "tool" or "harvesting tool" as used herein refers to any number of tools or end effectors that are capable of removing or harvesting follicular units ("FUs") from a body surface. It is understood that the body surface could be any area of the body having hair, a body surface can be attached to the body or may be a flap of skin or body tissue removed from the body. Such tools may have many different forms and configurations. In many embodiments, the tool comprises a hollow tubular shaft and thus may be labeled, for example, a cannula, a needle, or a punch. The terms "coupled," or "attached," or "mounted" as used herein, may mean directly or indirectly coupled, attached, or mounted through one or more intervening components.

Embodiments of the methods of the present invention may be implemented using computer software. Various programming languages and operating systems may be used to implement the present invention.

Manual hair harvesting procedures where individual follicular units are harvested using FUE technique are time consuming procedures as each individual FU is being separately harvested from the body surface. Even with the partially automated or fully automated harvesting procedures and systems, a certain time is required to make and execute various selection decisions when choosing the next FU to be harvested. The automatic selection system of the present invention is designed to increase the efficacy of the harvesting process in both manual and automated procedures, and it is especially useful, for example, in a robotic hair harvesting procedure.

Robotic hair transplantation systems and methods are described in the commonly assigned Published Patent Application US 2007/0078466 ("the Bodduluri et al. publication") which is incorporated herein by reference in its entirety. The above-mentioned application explains that the hair harvesting tool is carried on a movable (e.g. robotic) arm and the arm is repositioned each time after follicular unit is harvested to move and align the harvesting tool with the next follicular unit to be harvested under the guidance of the imaging system. Of course, each such movement, repositioning and realignment of the movable arm (and, therefore, the tool carried by the arm) takes times and increases the duration of the procedure as a whole. Therefore, it is highly desirable to design an efficient plan where movement and reorientation of the arm (and the tool) is minimized from one FU to another.

When harvesting hair follicles, it is desirable to align the harvesting tool with the follicular unit to be harvested. The better the needle to follicular unit alignment, the lower is the chance of hair transection, therefore, it may be ideal to aim for near perfect alignment between the needle and follicular unit (for example, having their respective axes parallel or at a certain desired small angle to each other). To achieve this goal, one potential policy or strategy to employ would be to pick an FU amongst a population of candidate FUs whose orientation most closely matches that of the previously harvested FU. In this manner the total movement of the robotic arm carrying the tool is minimized, which in turn minimizes the time to align, and consequently reduces the overall treatment time. Yet another alternative possibility is to simply pick the FU closest to the current location of harvesting tool, such as a needle or cannula.

In addition to pure consideration of the distance of the movement of the harvesting tool, the throughput of the overall procedure also depends on various additional factors that could be taken into consideration, such as the efficacy of the imaging and quality of the harvested follicular units. For example, potential FUs candidates for harvesting may be very close to a recent harvest site which, generally, would suggest them as very good candidates from the distance/timing point of view. However, if there was an excessive bleeding around any of them due to the prior immediate harvesting in that area, it is consequently preferred to avoid this region because excessive amounts of blood run a higher risk of confusing the associated image processing. Similarly, while being in close favorable position to the previous harvesting site, the potential candidate follicular unit may be too close to another follicular unit such that by harvesting the candidate FU, the neighboring FU may be damaged or transected. Moreover, due to clinical concerns, such as potential additional harvesting procedures in the future or a need to reduce scarring, the closest follicular unit may not be desirable. Therefore, such a candidate FU may have to be avoided (filtered out) despite its basic favorable proximity to the previous harvesting site.

It is noted here that due to patient variability and numerous factors affecting the procedure and potential future anticipated follow-up procedures, the best strategy may involve a combination of different "filters" and "policies". For example, the method may include one or several main policies for sorting available follicular units for harvesting, and in addition, the population of candidate FUs may be also filtered according to one or several criteria. For example, those FUs in close proximity to bloody portions of the scalp may be filtered. Then the remaining FUs may be sorted via a policy of preferring FUs close to the current needle position, and whose orientation matches the FU that was just harvested. As will be understood by those skilled in the art, a policy may be set up and/or described as a filter. However, regardless of how it is called, it shall fall within the scope of the present invention and shall be considered a policy if it is directed to selecting follicular unit(s) for harvesting. It should be noted that the system is runtime-configurable, meaning that each of the filters and policies can be turned on or off, depending on the clinical situation.

FIG. 1 is a block diagram of the exemplary automatic follicular unit selection process of the present invention. First, at step 100 a pool of candidate follicular units for harvesting is identified in one or more images of a surface containing follicular units. At step 110, follicular units from the pool are automatically sorted according to one or several policies. There may be only one policy, alternatively, there may be several different predetermined policies, some designed to improve speed of the procedure, some may be directed to efficacy, reduced hair transaction, and various additional goals, as described in more detail below. At step 120, a particular follicular unit to be harvested next is automatically selected as one of the best available follicular units according to the above policies. Block 130 is shown by broken line to indicate that it is an optional step to the method in its generic form. At step 130, an automatic filtering of follicular units based on some criterion is performed, for example, follicular units that do not meet one or more criteria are automatically filtered from the pool of candidate FUs. It should be noted that the filtering can be done either "negatively" by excluding certain hairs that fall, for example, within or outside a predetermined parameter or criterion, or "positively" by including only those hairs that either fall within or outside a predetermined parameter or criterion. Either of these approaches is contemplated by the present invention, therefore, any reference in the description and/or in the claims to a filtering by discarding follicular units according to a certain criterion automatically includes filtering by keeping follicular units outside of or opposite to that certain criterion. Many various filters could be used dependent on specifics of each situation as described in more detail below.

Figure 2:
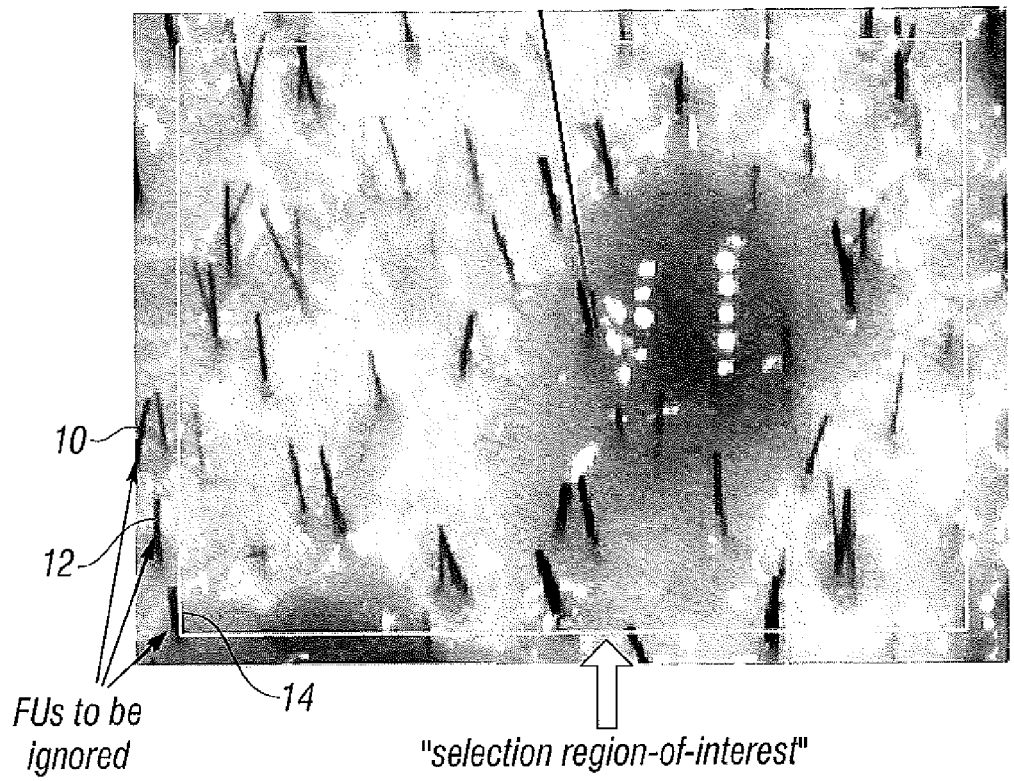
FIG. 2 is a print of a digital image of one exemplary filtering criterion according to an embodiment of the method of the present invention.

With reference to FIG. 2, a print of a digital image shows an example of selecting a region-of-interest by filtering FUs that could leave the field of view (FOV). More specifically, as seen in FIG. 2, FUs 10, 12 and 14 which are too close to the edge of the FOV are ignored/filtered, since there is a good chance that these FUs might be lost due to patient movement due to leaving the FOV. In FIG. 2, note that a selection of the region-of-interest (ROI) can be dialed up or down, depending on the amount of patient movement. Typical values for this "selection ROI" are 75% of the total area of the image frame.

Another example of the alternative filtering criterion is follicular units that have not been registered with the image processor for a minimum amount of time, for example, in a predetermined preceding time interval. When blood from a nearby wound (created by preceding harvesting of another follicular unit) is seeping into the region from which the next follicular unit is selected, it often may corrupt at least portions or certain frames of the image processing. As a result, a particular FU may be seen in one frame and then not being seen in a subsequent frame. Follicular units that are continually registered by the image processor are considered "stable" and, therefore, provide higher confidence for reliable harvesting. Therefore, it may be desirable in some situations to filter out FUs that are "not stable" or, putting it another way, filter in those FUs that are "stable" as explained above.

Yet another useful filtering criterion is a particular type of follicular units that are desired for harvesting or, to the contrary, should be avoided. For example, follicular units F1 and F2 are typically highly desirable, so the filter could be set up to ignore F3s and above ("don't care" type of filter), or it could be set up to select only F1s and F2s. Similarly, a filter that precludes hairs not of a minimum caliber, or width (typically at least 75 um) is useful for avoiding miniaturized or wispy FUs. "Wispy" hairs are characterized by a smaller than normal caliber, and are problematic when it comes to transections. Moreover, wispy hairs tend to have more image processing problems due to a greater propensity of getting lost amidst a constantly varying and busy scene.

Several additional examples of the filtering criteria are listed below. In many cases, measuring which way the FU is pointing relative to the scalp surface may be a key factor in orientation of the harvesting tool relative to the FU. There are certain cases where this measurement may be noisy (for example, due to blood or imaging noise because of light-colored or grayish hairs). As a result, it may be desirable to filter FUs that do not meet specified orientation stability criteria. In other cases, the filtering criterion is whether one FU is too close to another FU. "Too close" may be a function of the harvest needle diameter. If two FUs are close enough together, then extraction of one will very likely lead to transection of the neighbor. This is a situation best avoided, and therefore, the corresponding filter could be implemented.

Figure 3:
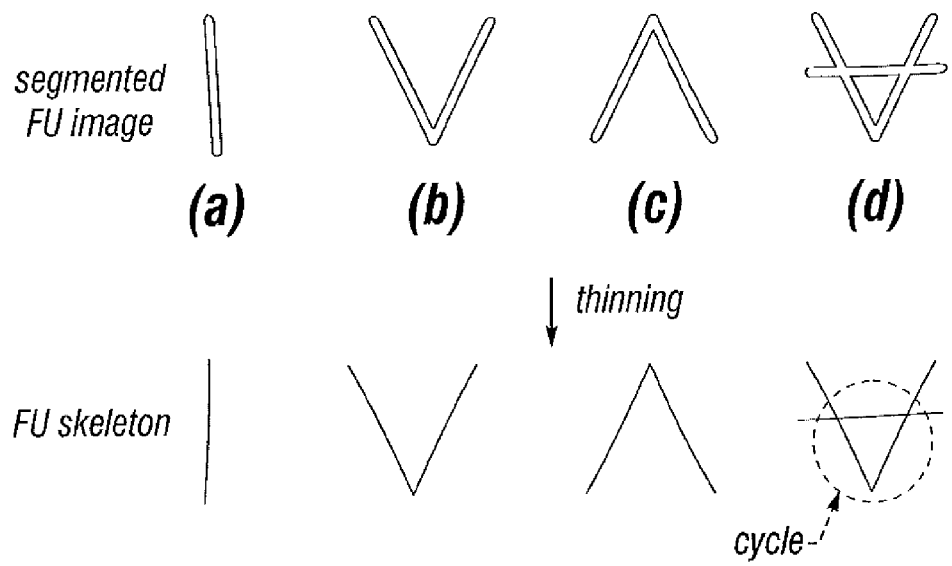
FIG. 3 is a schematic representation of another exemplary filtering criterion according to an embodiment of the method of the present invention.

Some FUs possess a complex shape, which is indicative of an FU that may cause problems during alignment with the harvesting tool. Better alignment results in more accurate FU extractions and reduction of the FU transaction rates. In light of that, one may prefer "simple" F1s or F2s over FUs having complex shape and configuration. "Simple" refers to FUs that have simple shapes. For example, the "V" shape is considered to be fairly simple amongst F2 shapes. FIG. 3 shows four representative segmented FUs (in the upper row of the figure), and their corresponding "skeletons" (in the lower row). Generating a skeleton or "skeletonization" is a process for reducing foreground regions in segmented image to a skeletal remnant that largely preserves the extent and connectivity of the original region of the image while discarding most of the original foreground pixels. This reduction of the foreground region occurs by peeling off a pattern of as many pixels as possible without affecting the general shape of the object being imaged. There are different ways of computing the skeleton of a segmented image. One exemplary approach is the thinning approach, where one successively erodes away pixels from the boundary while preserving the end points of line segments until no more thinning is possible (at which point what is left is the skeleton). As seen in FIG. 3, segmented image (d) is a F2 whose skeleton contains a "cycle" due to an uncut hair occluding a portion of the F2. Cycles and other noisy skeletal shapes derived from the segmented FU images make it more difficult to discern the major axis of the FU, which interferes with alignment of the tool to the FU. Therefore, one may want to exclude FUs whose morphology is not one of a straight line or curve, a V, or upside-down V. In one exemplary embodiment of the present invention, it is achieved by first pruning the skeleton (removal of "twigs") and then classifying FUs into "simple" and "complex" bins.

Figure 5A:
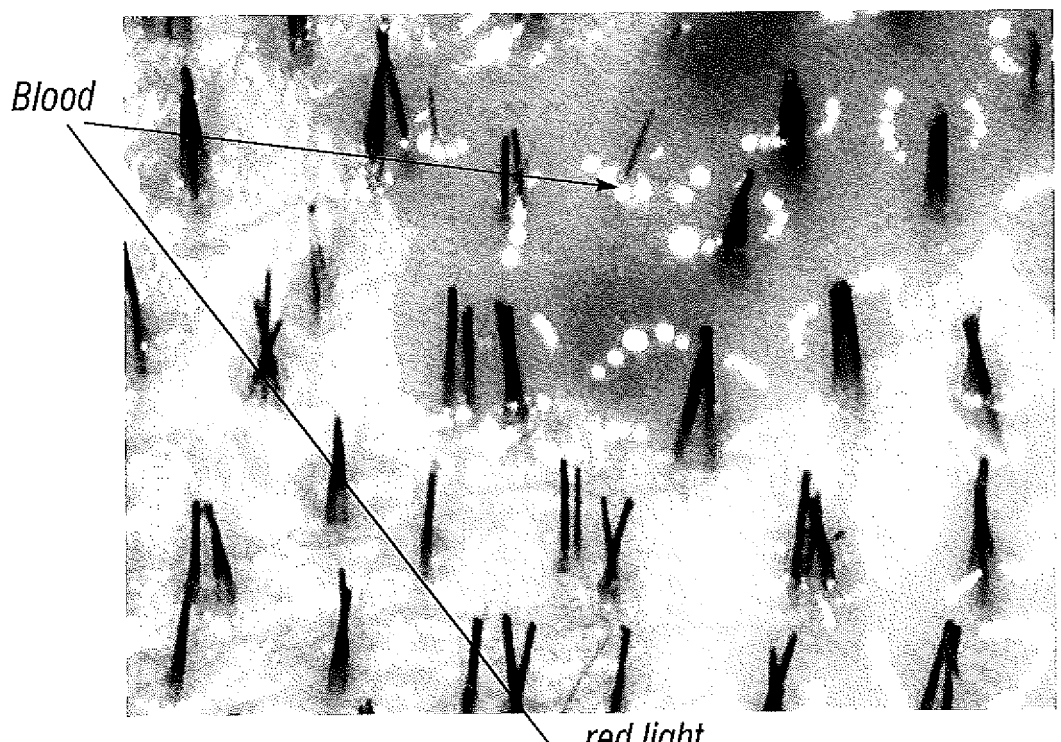
FIGS. 5A and 5B are prints of the exemplary digital images of the blood region (of FIG. 4) under red/white light.
Figure 5B:
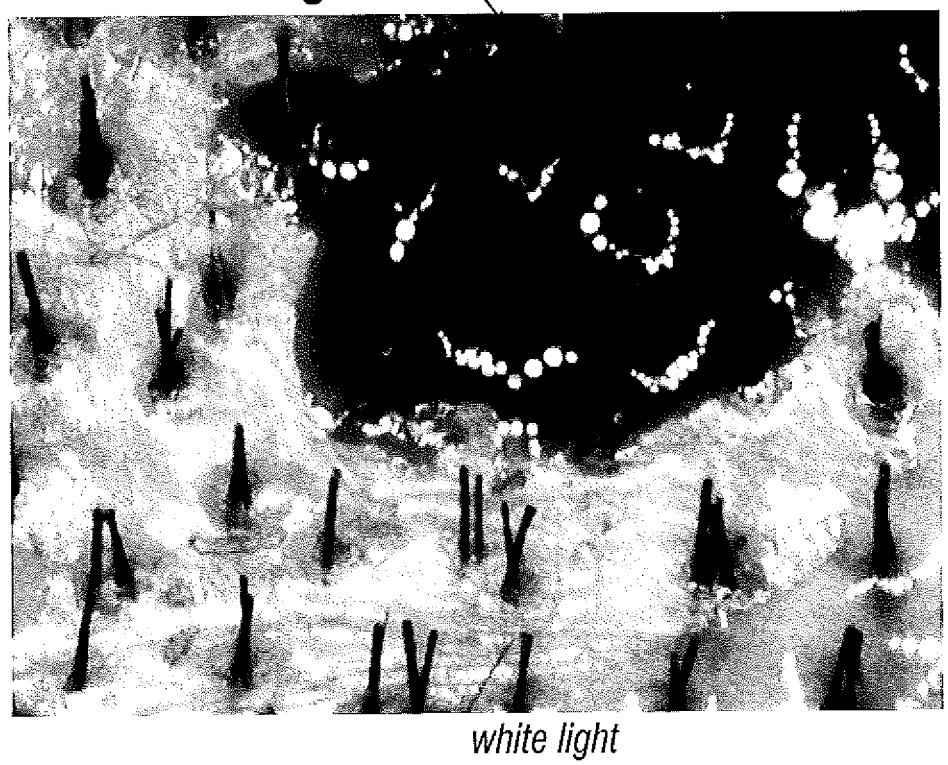

Further filtering criterion that is contemplated with the selection method of the present invention are FUs that are too close, or even lie within, bloodied or bruised regions of the body surface, such as a scalp. This typically means the FUs in question are too close to a recent harvest site. In order to minimize transection rates, it is desirable to maintain a given density of harvest sites, and this density is closely related to the harvesting punch diameter. Therefore, by identifying previously harvested sites through image processing, it is possible to spread out the FUs evenly within the donor area. Moreover, blood will tend to contaminate imaging measurements, so there are many various reasons to exclude those hairs which are too close to blood. FIG. 4 is an exemplary block diagram of the blood region detection and proximity check depicting one example of how the imaging and processing systems of the present invention ascertain which portions of the imaged scalp are bloody regions that should be avoided. During the exemplary process as shown in FIG. 4, at step 200 one or more images of the area of interest or FOV using white light are taken, which highlights blood (at the expense of hair, due to excessive glare and reflection). The motivation of this "white flash" can be noted in FIGS. 5A and 5B where the blood is much more obvious under white light than under red light. Also, one or more images of the area of interest or FOV using red light are taken to highlight follicular units, as seen in FIG. 5A. Of course, the order of taking pictures using white and red light is not important. At step 210, images taken at step 200 are processed. The images taken under the red light may be processed, for example, according to the FU counting and classification techniques described in commonly assigned co-pending published applications WO 2008/024954 and WO 2008/024955. Processing of the images taken under the white light may include, for example, various segmentation techniques and steps (as known in the art), including by way of example and not limitation fixed thresholding followed by post-processing binary erosion. At step 220, the areas containing blood are determined and, for example, a list of bloody areas may be generated. At the same time, as a result of the processing of the images containing follicular units, the list of follicular units within the same area of interest of FOV may be generated as well. At step 230, a proximity check is performed. From the pool of candidate FUs, those hairs which are found to be too close (typically within 10 pixels) in relation to a "blood region" are excluded from the selection process. Again, this filtering can be done either "negatively" by excluding those hairs that are within certain range of pixels from the bloody region or "positively" by including only those hairs that are outside the above range. Only those FUs that pass the proximity check will be harvested, or will be considered for harvesting under additional policies and selection criteria that may be further employed.

One exemplary mechanism by which one can measure where in the "white flash" image the blood is prevalent is via a variance filter. FIG. 6 shows such exemplary blood detection using a variance filter. As could be seen from FIG. 6, bloody regions are characterized by little to no texture (low image variance) while non-bloodied regions of the imaged portion of the body surface, such as scalp, contain comparatively greater amounts of texture (high variance). Also, because there is some delay between the "white flash" and the normal red-field image (that may be on the order of, for example, two thirds of a second), the patient may move during even that brief time. Therefore, to increase the accuracy of the measurement, it is recommended to register the white flash image against the red-field image.

Another approach is to enhance the image such that the hair can be visualized despite the presence of blood and/or other fluid. There may be clinical concerns that could dictate that hair in these regions be avoided, or could provide motivation for excluding hair from the candidate pool, however such image enhancement may serve to otherwise enlarge the candidate pool available prior to applying the above-described filtering criteria.

In order to improve visibility of hair on a skin surface in a region that is at least partially bloodied or bruised, and maybe expand the potential candidate pool, it may be desirable to subdue or suppress the blood in the image, thereby enhancing the visibility of the hair, for example, when it is partially covered by blood. It may also be desirable to make the color of the blood in the image substantially match the color of the skin in the image, thereby reducing or minimizing the contrast between the image of the blood and the image of the skin surface, for example, to zero or to a very small contrast value.

Since the color of blood and the color of skin varies from one person to another (and therefore so do images of the same), selection of an appropriate wavelength of light for illumination purposes is not a trivial matter. There is no single uniform wavelength of light that can be used to illuminate blood whereby the contrast between the imaged blood and the imaged skin surface without blood will be minimized. When harvesting hair follicles, rather than accepting the contrast attained by using a single light source, or going through the tedious process of manually changing the light source used during the imaging process until an image with the desired contrast is obtained, this embodiment of the invention provides a light source having at least two substantially monochromatic emitters, which between them cover a spectrum of color suited for this purpose (as used herein, light sources such as LEDs and SLEDs are considered to be substantially monochromatic emitters). The purpose being to reduce the contrast between the image of the blood and the image of the skin surface that does not contain blood, for a wide range of blood color and a wide range of skin color, and to do so in such a way that allows either to visualize hair that was not previously seen (because, for example, it was partially covered with blood), or to improve visibility of a hair graft that was insufficiently visible to allow, for example, to harvest it. Control of the intensity of various regions of the illumination may also aid in accentuating hair follicle(s) features, which in turn improves the ability to locate hair follicle(s) and in some embodiments to better track the movement of the patient and hair follicles.

Figure 11A:
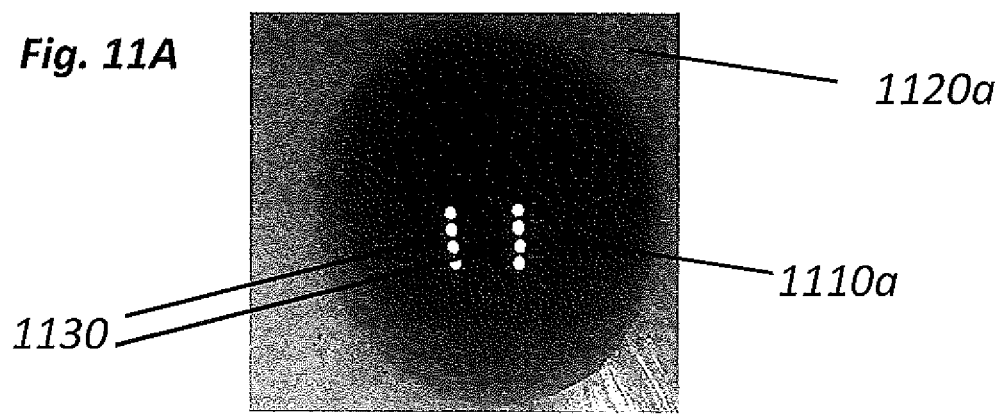
FIGS. 11A-C are prints of examples of digital images acquired of a blood region using different wavelengths of light.
Figure 11B:
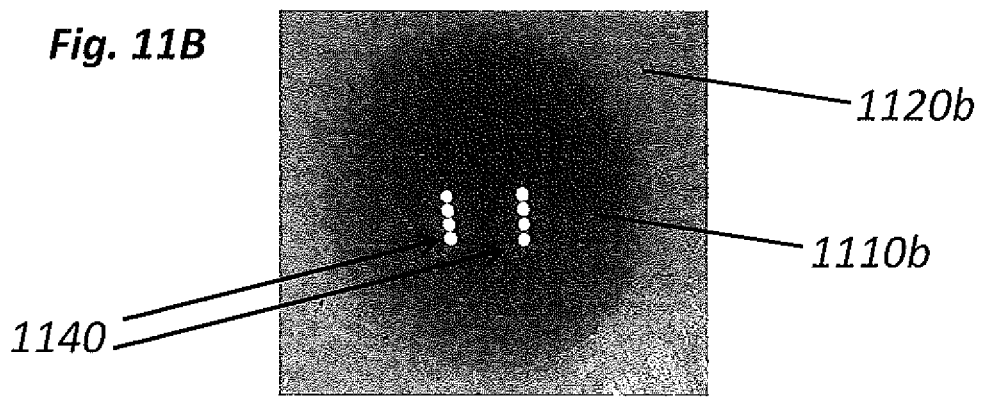
Figure 11C:
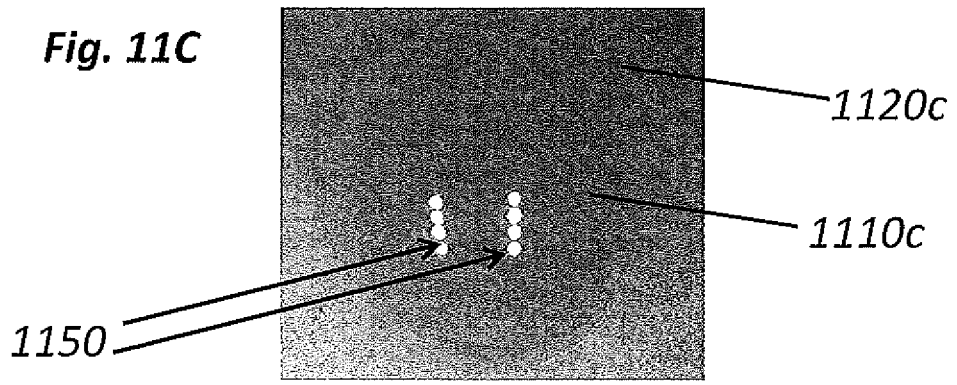

FIGS. 11A-C illustrate images obtained of blood on a skin surface, all three images having been generated using red light under different illumination conditions. FIG. 11A illustrates an image of blood 1110a and an image of a skin surface 1120a that was generated by illuminating the skin surface with a red light source 1130 having by way of example a wavelength of about 630 nm. FIG. 11B illustrates an image 1110b, 1120b generated by illuminating the same blood on the same skin surface with a red light source 1140 having in this example a wavelength of about 680 nm, and FIG. 11C illustrates an image 1110c, 1120c generated by illuminating the same blood on the same skin surface with a red light source 1150 having in this example a wavelength of about 735 nm. It can be seen that in each case, the contrast between the image of the blood and the image of the skin surface is quite different, being in those examples substantially larger in FIG. 11A than in FIG. 11C. It can also be seen that the shade of gray of the image of the blood and the image of the skin surface are also different in each of the images.

In one embodiment of the invention, the illumination source used for imaging may comprise at least two red light emitting diodes (LEDs), the LEDs selected to emit light at defined ends of the spectrum desired, for example a first LED with an emission band that peaks at a wavelength of about 630 nm (or, e.g., between 640 nm and 690 nm) and second LED with an emission band that peaks at a wavelength of about 740 nm (or, e.g., between 685 nm and 790 nm). By altering the relative contributions of the two emission bands, that is by altering the intensity of each, and combining the two emission bands of the LEDs together, a color characteristic of the combined total emission may be generated which exhibits a shade of color that may be different from the color associated with either of the original peaked wavelengths. That will effectively create a red light source having a third wavelength, having a value that lies in this example between about 630 nm and about 780 nm. It will be appreciated that other light emitting devices may be utilized for this purpose, such as, for example, superluminescent diodes (SLEDs).

Figure 12:
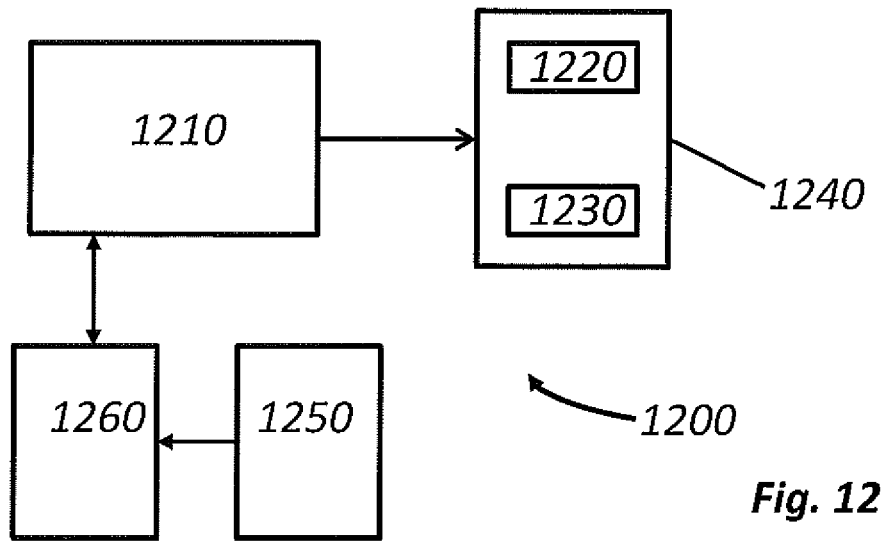
FIG. 12 is a block diagram illustrating a system according to an embodiment of the invention.

FIG. 12 illustrates an illumination system 1200 according to an embodiment of the invention which enables the relative contributions, or intensities of at least two above-mentioned LEDs to be varied or controlled for the imaging purposes previously described. The illumination system 1200 comprises a controller 1210 for controlling operation of two LEDs 1220 and 1230 (schematically shown by example), and enabling the relative contribution, such as the intensity, of each LED to be varied accordingly. For example, the controller 1210 may be configured to first turn on the first LED 1220, the one whose emission band peaks at the lower wavelength of 630 nm at a first contribution value, and turn on the second LED 1230, the one whose emission band peaks at the higher wavelength of 780 nm at a second contribution value. The two contribution values may be the same or different. The emission bands emanating from the LEDs 1220 and 1230 are combined by means known to those skilled in the art and therefore do not need to be described here, and light generated by the light source 1240 has an emission band that peaks at a third wavelength, this third wavelength exhibiting a different shade of red than that of either the first or the second LED alone. While the skin surface is illuminated with the generated light emitting at this third wavelength, an imaging device 1250 acquires a first image of the skin surface having blood on at least a portion of it. A processor 1260 may be configured to process this first image generated, and to determine the presence of a contrast between the image of the blood and the image of the skin surface without blood, assuming there is one. This identification may be accomplished, for example, automatically, including in absolute terms, or merely a determination of a difference between the intensity in the image between the blood and the skin surface. In the alternative, the determination may be done manually, for example, the operator of the system may make such determination.

The contribution values of the two LEDs 1220 and 1230 shown by example in FIG. 12 can be adjusted, if required, by the controller 1210 until the contrast between the image of the blood and the image of the skin surface without blood is the desired value, for example, substantially close to zero. At this point, visualization of a hair graft that might be in the vicinity of blood can be improved or enhanced, and the candidate pool may be expanded. Having improved the visualization of the hair graft, it will make much easier to perform any maneuvering or operation on such hair graft, for example, harvesting it. After the hair graft has been harvested, the contribution values of the two LEDS may optionally be adjusted such that visualization of a location from which the hair graft has been harvested can be enabled, prior to harvesting a subsequent hair graft. For example, the previously suppressed blood in the area where the hair graft has been harvested may be restored or made visible again, for example, with the use of the controller 1210 and/or the processor 1260, or alternatively with the use of different controllers and/or processors. In this manner, areas from which hair has already been harvested can be avoided, and excessive depletion of a donor area can be prevented.

Figure 13:
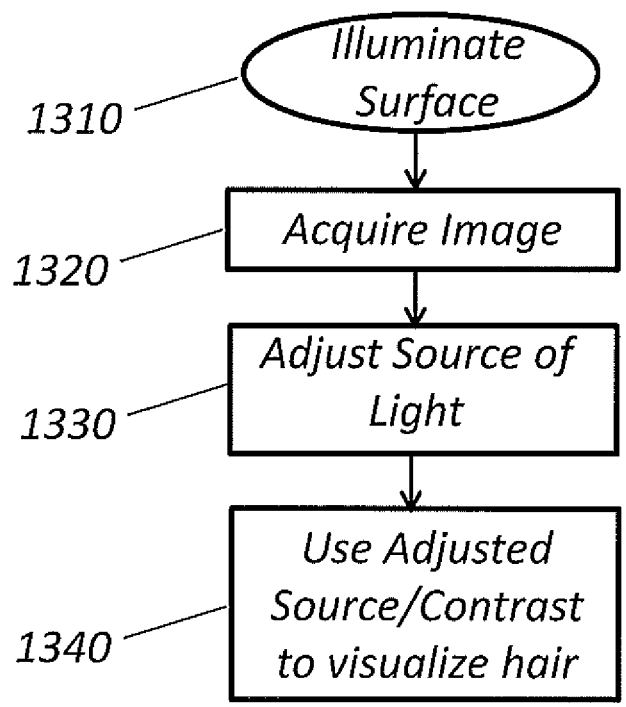
FIG. 13 is a flow diagram of an embodiment of the method of the invention.

FIG. 13 is a flow diagram of an embodiment of a method for improving visualization of hair for use in hair transplantation. The illustrated example of the method starts with illuminating with a light source a skin surface having blood on a portion of the skin surface (in 1310), and acquiring an image (in 1320). The illumination step may be accomplished anywhere on a skin surface, for example, on the scalp of a patient or on any other skin surface area of the body where subsequent enhancement of hair visualization, for example, for harvesting will be performed; alternatively, the illumination step may be conducted in a region of a skin surface different from the region where subsequent hair visualization will be performed. The image acquired comprises a portion of the skin surface without blood as well as a portion of the skin surface with blood thereon. As shown in 1330, a wavelength of the light source is adjusted such that when illuminated with this selected adjusted light source, the contrast between the image of the skin surface without blood and the image of the blood is minimized. Minimization in the context of the present application means that the contrast between the image of the skin surface without blood and the image of the blood is substantially suppressed such that the image of blood appears to blend in or at least insignificantly differ from the image of the skin surface that does not have blood thereon. In some embodiments, the contrast may be reduced to zero (making the blood and the skin surface generally substantially undistinguishable). In some embodiments, however, it is not necessary to reduce the contrast to zero, but rather make it small enough to enable visualization of a hair graft that might be in the vicinity of blood, or improving or enhancing visualization of the hair at least partially blocked by blood in the area.

Adjustment step 1330 may optionally require that one or more additional images be acquired to verify that the contrast between the image of the skin surface without blood and the image of the blood have been minimized as desired. The adjustment step 1330 may require in certain embodiments the repeated adjustment of a wavelength of the light source and acquiring associated images until a value of the wavelength has been reached which provides the desired minimization in contrast. Alternatively, the adjustment step 1330 may comprise referring to a database to provide the wavelength adjustment required. The database may, for example, comprise a look-up table based on skin and blood colors, information of wavelength adjustments and the associated changes in contrast between imaged blood and imaged skin surfaces, or may be patient specific information acquired at any time prior to the time that this information is used to improve hair visualization, or other such related information.

As shown 1340, the adjusted light source (to minimize the contrast as explained above) is used to visualize a hair graft located in a region of a skin surface having blood thereon. As previously stated, the hair graft which is visualized may be located in the same region, or a region close to the region that was originally illuminated in 1310 and imaged in 1320. Alternatively, the hair graft may be located in another region, for example in a region that contains hair to be harvested for transplantation purposes while the illumination and adjusting contrast could have been done in a different region of the skin surface that was used for initial calibration and contrast determination. For example, an area of a skin surface (regardless of whether it has hair or not) could be punctured to have blood appear on the skin surface, so that the necessary imaging and desired contrast calibration could be determined for a particular patient. If the hair to be visualized is located in a region other than that imaged in step 1320, it may be advantageous to ensure that the skin surface imaged in step 1320 and the skin surface in the region it is desired to visualize hair are substantially similar in physical appearance, including color. In the case of persons with discolored, tanned or diseased skin, for example, it may be desirable that the region of the skin imaged for the purpose of ascertaining the adjustment required to the light source to reach the desired minimum contrast, share similar discoloration, tanning, or disease criteria to that of the region where it is desired to visualize hair. In addition, if topical applications have been applied to one region, it may be desired that they be applied to the other.

To ensure that the most appropriate wavelength of light is selected for imaging the blood on the skin surface, for the purposes of hair harvesting, the lighting arrangement described above can be modified, with the values of the at least two LEDs and/or their relative contributions varied until a desirable contrast between the image of the blood and the image of the skin surface is achieved. In practical terms, it is desirable that the contrast between the image of the blood and the image of the skin surface without blood be substantially small, in some embodiments close to zero, such that the image of the blood and the image of the skin without blood would sufficiently match each other or blend together. As a result, the visibility of the hair follicles or follicular units will be enhanced against that "blended blood/skin" background, or in certain cases, the previously invisible hair will be visualized. The modification or adjustment of the light source can be carried out manually by an operator, or the system can be calibrated to enable appropriate selection. Calibration provides an indication of the image contrast attainable between the blood and the skin surface by utilizing the spectrum of color light emission available from the relative contributions of the LEDs. Thus an operator is able to select the appropriate contribution ratio to enable selection of the desired contrast between the image of the blood and the image of the skin surface, such that visualization of a hair follicle on the skin surface is enhanced. That in turn aids in the hair harvesting procedure. Once a hair has been visualized and harvested, a wavelength of the light source may optionally be adjusted such that visualization of a location from which the hair graft has been harvested can be enabled, prior to harvesting a subsequent hair graft. For example, the previously suppressed blood in the area where the hair graft has been harvested may be restored or made visible again. In this manner, areas from which hair has already been harvested can be avoided and excessive depletion of a donor area can be prevented. In an alternative, the system itself is able to use the calibration data to select the appropriate contribution ratio to enable selection of the desired contrast between the image of the blood and the image of the skin surface, such that visualization of a hair follicle on the skin surface is enhanced.

Figure 14:
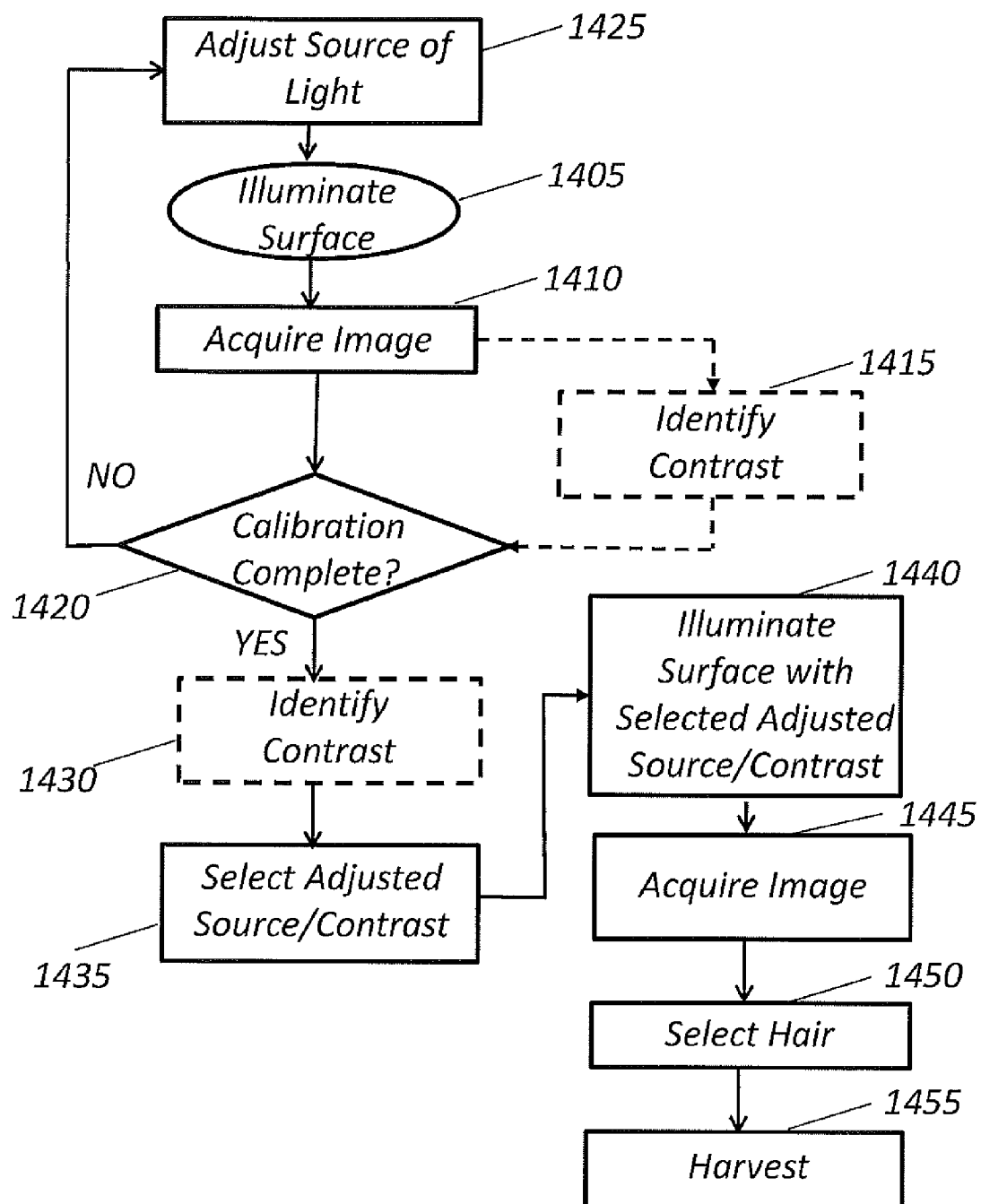
FIG. 14 is a flow diagram illustrating an example of an automated routine according to an embodiment of the method of the invention.

The calibration may be automated. FIG. 14 is a flow diagram of an embodiment of an automated process using, for example, the system similar to that depicted in FIG. 12. In step 1405 the skin surface having blood on a portion thereof is illuminated with a light source 1240. In this particular example, a light source 1240 comprises two LEDs 1220, 1230, the first LED 1220 with an emission band that peaks at a wavelength, by way of example, of about 680 nm and second LED 1230 with an emission band that peaks at a wavelength, by way of example, of about 735 nm. In step 1405, the LEDs 1220, 1230 are operated by controller 1210 such that the first LED 1220 contributes, for example, 100% of the light emitted, and the second LED 1230 contributes 0% of the light emitted. The light emanating from the light source 1240 therefore having a wavelength that peaks at around 680 nm. In step 1410, while the skin surface is illuminated with the source of light operated in this manner, an image acquisition device 1250 may acquire an image of the skin surface having blood on a portion thereof. Optionally, at this stage, a processor 1260 may process the acquired first image and determine in step 1415 the presence of a contrast between the image of the blood and the image of the skin surface, and optionally determine a value associated with this contrast. Alternatively, the calibration process may continue, with the determination of the presence of a contrast being carried out at a later stage 1430, for example when a range of various contribution values of the LEDs has been cycled through.

After acquisition of the first image, the processor 1260 determines if the calibration cycle has been completed, in step 1420. If it has not been completed, in step 1425 the controller 1210 adjusts the contribution of the first LED 1220 to a lower intensity value, for example 90%, and the contribution of the second LED 1230 to a higher intensity value, for example 10%. Adjustment of the contribution values in step 1425 may be facilitated by adjusting the intensity of the LEDs. With the LEDs 1220, 1230 in this second mode of operation, the light emitted from each LED is mixed and the diffused light emanates (step 1405) from the light source 1240 having a different wavelength, that of the combined light, and a second image is acquired (step 1410) of the skin surface having blood on a portion thereof, while the skin surface is illuminated with this adjusted light source 1240. The processor 1260 can once again process in step 1415 this second image generated and determine the presence of a contrast between the image of the blood and the image of the skin surface. Alternatively, the calibration process may continue, with the identification in contrast being carried out at a later stage, in step 1430 for example, when a range of contribution values of the LEDs has been cycled through.

The process of adjusting the contribution or intensity (step 1425) of the first and second LEDs 1220 and 1230, combining the emitted light to provide differing wavelengths of emission to illuminate the skin surface (step 1405), acquiring an image (step 1410) of the skin having blood on a portion thereof, and processing the image to determine a measurement of contrast between the image of the blood and the image of the skin surface (steps 1415 or 1430) may be repeated as many times as desired until the calibration process is complete. During this time, for example, the intensity of the first LED may be stepped down in intensity in 10% steps (or any other percentage steps) from 100% to 0% and the second LED may have been stepped up in intensity in 10% steps (or any other percentage steps) from 0% to 100%. At the end of this process, the processor 1260 has acquired information on a series of intensity or contribution values associated with each of the first and second LEDs 1220, 1230 and the contrast that results between the image of the blood and the image of the skin surface when these various contribution values are applied.

Armed with this information, in some embodiments the operator is able to select in step 1435 the most appropriate contribution values, or intensities of the first and the second LEDs 1220, 1230 to illuminate (step 1440) the skin surface such that an image is acquired in 1445 in which the contrast between the image of the skin surface and the image of the blood is minimized. Based on this enhanced image, the operator is able to select (step 1450) the at least one hair follicle and, optionally, to harvest it (step 1455). As mentioned earlier, alternatively, the processor itself may be programmed to make such a selection, and to also provide instructions to the controller to control the first and second LEDs to emit radiation of the required intensity. In some embodiments, any one or all steps 1440, 1445, 1450 and 1455 may be partially or fully automated.

It will be apparent that the number of steps that are utilized for such a calibration is not limited to those described above. Also, the method does not require that all of the described above steps be present, so that in some embodiments of the method some of the above-described steps are omitted. Such a calibration may comprise simply a selection from two settings, the first setting being the first LED operated at 100% and the second LED operated at 0%, and the second setting being the first LED operated at 0% and the second LED operated at 100%. Alternatively the calibration can contain any number of calibration points, the points being spaced in any manner desirable, whether that be based on the intensity of the individual LEDs or the variation of color achieved, for example. In addition, the order of the steps identified in connection with FIG. 14 is implementation dependent, and could be performed in a different order, have various steps combined, or have the steps shared between more that one processor, for example.

FIG. 7 illustrates additional filtering criterion that could be used in a selection methodology according to the present invention. Sometimes, images of the objects in two different views (for example, from left and right cameras where stereo cameras are used) do not appear the same. One example of such situation is shown in FIG. 7 where two separate FUs can be easily identified in one image of the stereo pair (in this case the left image), while in the corresponding other stereo image the two segmented FU images have morphed into a single object. This scenario is typically encountered in high-density areas of the scalp where the hairs might be longer than 2-3 mm, and the combination of the tool vantage point (and by extension the camera axis) and imaging noise prevent the FUs from being imaged as completely separate in both left and right stereo views. While generally more advanced imaging systems are capable of "virtually splitting" the FUs where they have morphed together; the tracking of such hairs can be more burdensome and problematic due to the asymmetric views from the left and right cameras. As a result, to simplify and speed up the process of hair harvesting, one may choose to exclude these FUs altogether and prefer to harvest the easier ones. As will be appreciated by those skilled in the art, many other filtering criteria may be implemented with the method of the present invention. These various criteria may be used individually or in numerous combinations depending on the specific needs and conditions in each harvesting case. As was previously mentioned, any of the filtering criteria may be turned "on" or "off" as desired.

Returning now back to FIG. 1, after the image has been enhanced and/or FU filters have been applied, there remains a set of filtered candidate FUs from which one can choose a certain number for harvesting. This selection block accomplishes this task by sorting the candidates based on one or more of the policies. There may be a variety of different policies chosen in an embodiment of a method of the present invention. In some situations only one policy (N=1) may be chosen, in other situations it could be a combination of a plurality of policies (N>1). As the policies could be turned "on" or "off," only active policies (those that are "on") will be followed. Below are listed some non-limiting examples of the useful policies.

To improve the speed and reduce the time of the procedure, one may choose a policy based strictly on the distance between the candidate FU and the position of the harvesting tool. In other words, the policy may be to pick the FU that is closest to the tip of the harvesting tool (which could be a needle, a cannula, a punch, and any other appropriate tool). Another alternative policy may be based on the amount of adjustment needed to align the tool with the FU so that the system will choose that FU whose orientation most closely matches the orientation of the FU that was just previously harvested. This way, the orientation of the tool does not need to be changed which will accelerate the entire process. The exemplary policies provided above are predicated solely on maximizing the throughput of the system, however, other considerations may govern the policy selection as well. For example, the policy may be based on improving the quality of the harvested hair, reducing transaction rates and similar considerations. One example of such policy is a selection of the FU whose emergence angle off the scalp or other relevant body surface is the greatest amongst a pool of candidates. The premise of this policy is that it is known that transection rates are lowest when the FU of interest points straight up with respect to the body surface rather than lying along the surface or having a very small emergence angle. The needle or other harvesting tool usually tends to skip and slide across the scalp when the FU in question lies flat, therefore, the above policy will increase the chances of correct alignment and operation of the tool in harvesting FUs with larger emergence angles.

In some embodiments of the present invention, one may choose a combination of any of the three exemplary policies mentioned above, or any other policies. This is achieved by assigning certain weight to each policy (a variable) and then scoring candidates FUs as a weighted sum of variables. Note that a particular policy may be assigned a zero weight in some instances so that it will not be included into consideration. If all three above-mentioned policies are taken into consideration, then in this example the score of each considered FU will be determined as follows:

FU score=(alpha)(distance to needle)+(beta)(delta from previous FU's orientation)+(gamma)(emergence angle)

wherein alpha, beta and gamma are "weight" assigned to each policy.

When automation is performed with a large number of FUs, multiple images of various locations on a body surface may be taken, including in multiple fields-of-view, so that a super-set of candidate FUs could be generated. This super-set is then used as an input "Candidate FUs" in block 100 of FIG. 1, and the subsequent process is similar to that described with reference to FIG. 1 as if only a single FOV was used.

According to another aspect a method of selecting an order of harvesting of follicular units is based on another policy that is designed to plan ahead for any potential future hair harvesting procedures that may be required for the same patient. It has been determined that certain individuals may require several hair transplantation procedures over the course of their lives. In some situations, they may need additional procedures because they will continue to lose hair and may need a repeat after a certain number of years. In some cases, the multiple procedures spread over a certain period of time are planned ahead of time by physicians and patients. In contemplation of the future procedures where additional hair may need to be harvested from the same general area, for better aesthetic results one may want to space out follicular units that will be harvested during the first procedure. That way, when more hair will be later harvested during the subsequent procedure, the donor area will still look full, even and natural. The premise behind this policy is to take into account the desired yield for the current procedure, while also remaining cognizant of any future procedures.

Figure 8A:
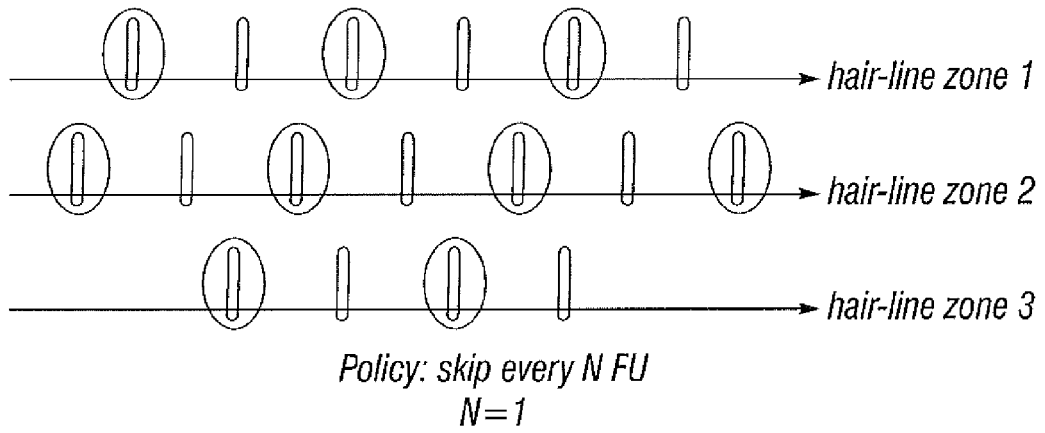
FIG. 8A is a schematic representation of an exemplary selection policy according to an embodiment of the present invention.
Figure 8B:
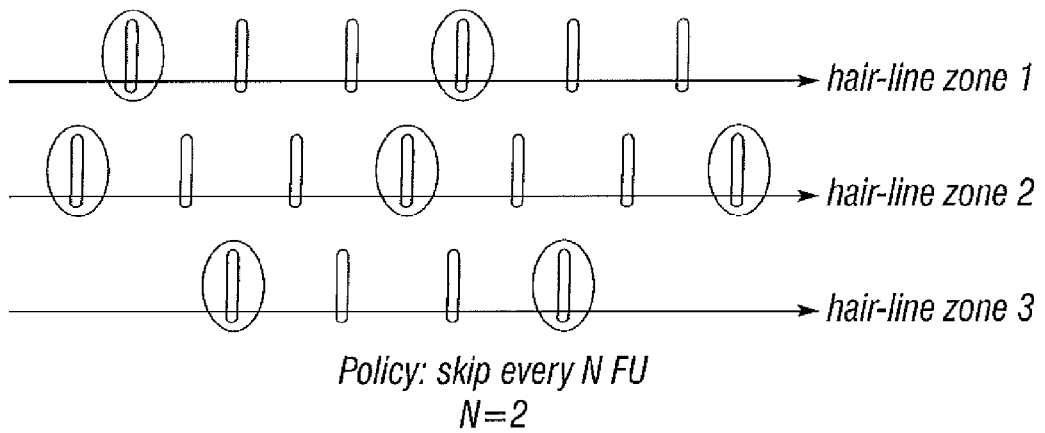
FIGS. 8B-C are schematic representations of alternative exemplary selection policies according to an embodiment of the present invention.
Figure 8C:
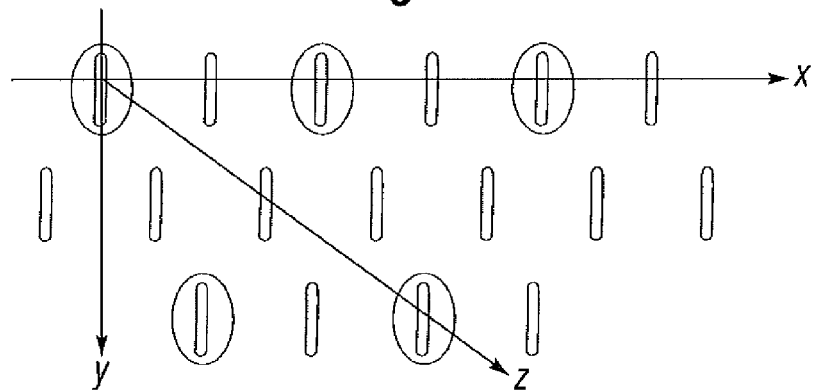

With reference to FIGS. 8A-C, it is described now an example of an embodiment of the method of the present invention based on multiple procedure planning policy. For example, to address the issue described above, one exemplary policy is to skip every $N^{th}$ follicular unit in a given pool of candidate follicular units. FIG. 8A shows the "skip policy" on a donor area, such as a scalp, where N=1. In other words, every other follicular unit is chosen for harvesting. The circled FUs represent selection of every other FU in a given hair-line zone. In the example of FIG. 8A, it is linear hair-line zones 1, 2 and 3. As could be seen from FIG. 8A, the total number of harvested FUs is 9. In this example, after the first procedure is completed, every other FU in the selected hair-line zones will be harvested. Such policy will work if no significant additional harvesting is anticipated in the same hair-line zones.

If it is necessary to remove more hair from the same zone or area in the future, it will be advisable to skip a plurality of FUs between each harvested FU in order to prevent large gaps between the remaining FUs. FIG. 8B shows a policy where a physician has taken into account future procedures in the same donor area and instead selected to dial N=2 into this policy. As a result, every two FUs were skipped so that the total number of FUs chosen for harvesting is now 7 instead of 9 of FIG. 8A. In the examples of FIGS. 8A-B the spatial grouping of FUs was performed in a linear fashion and in the same direction for hair-line zones 1, 2 and 3, however, the present invention is not limited to such linear unidirectional selection. For example, a skipping pattern for follicular units may be chosen from one or more various planning templates. Some exemplary skipping patterns may include one or both unidirectional and linear template of selecting every $N^{th}$ follicle in a hair-line. However, there is nothing preventing the applicability of this policy using multidirectional and non-linear selections, including other groupings, for examples patches or clusters, as shown by example in FIG. 8C along 3 exemplary directions x, y and z. 15.

Any of the systems and methods for selecting follicular units for harvesting, as described herein, may be used in conjunction with the robotic systems for hair harvesting and transplanting similar to those described in the Bodduluri et al. publication. For instance, the system described in the Bodduluri et al. publication may be programmed and configured to perform the methods of selecting a follicular unit according to the present invention. FIG. 9 is a schematic perspective view of one such exemplary robotic system 20 for hair harvesting (and, optionally, implanting). The system 20 includes a robotic arm 22 and an assembly 24 mounted, for example, for rotation on a down tube 26 of the robotic arm. Various arrows are shown to illustrate the movement capabilities of the system 20. Various motors and other movement devices may be incorporated in the assembly 24 to enable fine movements of an operating tip of a tool 28 in multiple directions. The exemplary robotic system 20 further includes at least one imaging acquisition device 29, which is described in more detail below. The image acquisition device may be mounted in a fixed position, or it may be coupled (directly or indirectly) to a robotic arm or other controllable motion device. The operating tip of the tool 28 is shown positioned over a body surface 30, in this case a part of the patient scalp having hair follicles thereon. The tool 28 is any number of harvesting tools useful for removing follicular units from the body surface 30.

A processor 32 of FIG. 9, comprises an image processor for processing images obtained from the image acquisition device 29. The processor 32 may also instruct the various movement devices of the robotic arm 22 and the assembly 24, including the harvesting tool, and act, for example, through a robotic control 34 as schematically shown in FIG. 9. The robotic control 34 may be operatively coupled to the robotic arm and configured to control the motion of the robotic arm, including the motion based on the images or data acquired by the image acquisition device. Alternatively, robotic control 34 may be incorporated as a part of the processor 32, so that all processing and controls of all movements of all the tools, including harvesting tools, the robotic arm and any other movable parts of the assembly, including those based on the images or data acquired by the image acquisition device, are concentrated in one place. The processor 32/controller may also be configured to instruct the adjustment of the light source to enhance the visualization of hair grafts on skin surfaces having portions with blood, as explained and described in reference to FIGS. 11-14. The system 20 may further comprise a monitor 35, keyboard 36, and mouse 38. A magnified image of the body surface 30 can be seen on the monitor 35. In addition, the system may comprise other tools, devices and components useful in harvesting, and/or implantation of the FU, or in hair treatment planning.

Some non-limiting examples of an image acquisition device 29 shown in FIG. 9 include one or more cameras, such as any commercially available cameras. The image acquisition device may take still images, or it could be a video recording device (such as a camcorder) or any other image acquisition device. While stereo or multi-view imaging devices are very useful in the present invention, it is not necessary to employ such geometries or configurations, and the present invention is not so limited. Likewise, although it is preferred that the image acquisition device be a digital device, it is not necessary. For example, the image acquisition device could be an analog TV camera that acquires an initial image which is then processed into a digital image (for example, via an analog-to-digital device like a commercial-off-the-shelf frame grabber) for further use in the method of the present invention. The image acquisition device may be coupled to a processing system, shown incorporated in the processor 32 in FIG. 9, to control the imaging operation and process image data. The image processor for use in the present invention may comprise any suitable device programmed and configured to perform the method of selecting FU for harvesting and the method for improving visualization of hair as described in present application. In one exemplary embodiment, the image processor for selecting FU is configured for identifying a pool of candidate follicular units for harvesting in one or more images obtained from an image acquisition device; automatically sorting FUs in the pool of candidate follicular units based on one or more policies (such as those designed to improve speed, quality, or efficacy of the hair harvesting); and automatically selecting a particular follicular unit to be harvested next, wherein a selected follicular unit is one of the best available follicular units based on the at least one or more policies.

By way of example, and not limitation, a suitable image processor may be a digital processing system which includes one or more processors or other type of device. For example, an image processor may be a controller or any type of personal computer ("PC"). Alternatively, the image processor may comprise an Application Specific Integrated Circuit (ASIC) or Field Programmable Gate Array (FPGA). The image processor may also include memory, storage devices, and other components generally known in the art and, therefore, they do not need to be described in detail here.

The image processor for selecting follicular units could be used in conjunction with various manual, partially automated and fully automated (including robotic) hair transplantation and treatment systems and devices, including but not limited to systems for hair harvesting, or hair transplantation. Similarly, the image processor of the present invention could be used with hair classification systems, or with hair treatment planning systems.

Figure 10:
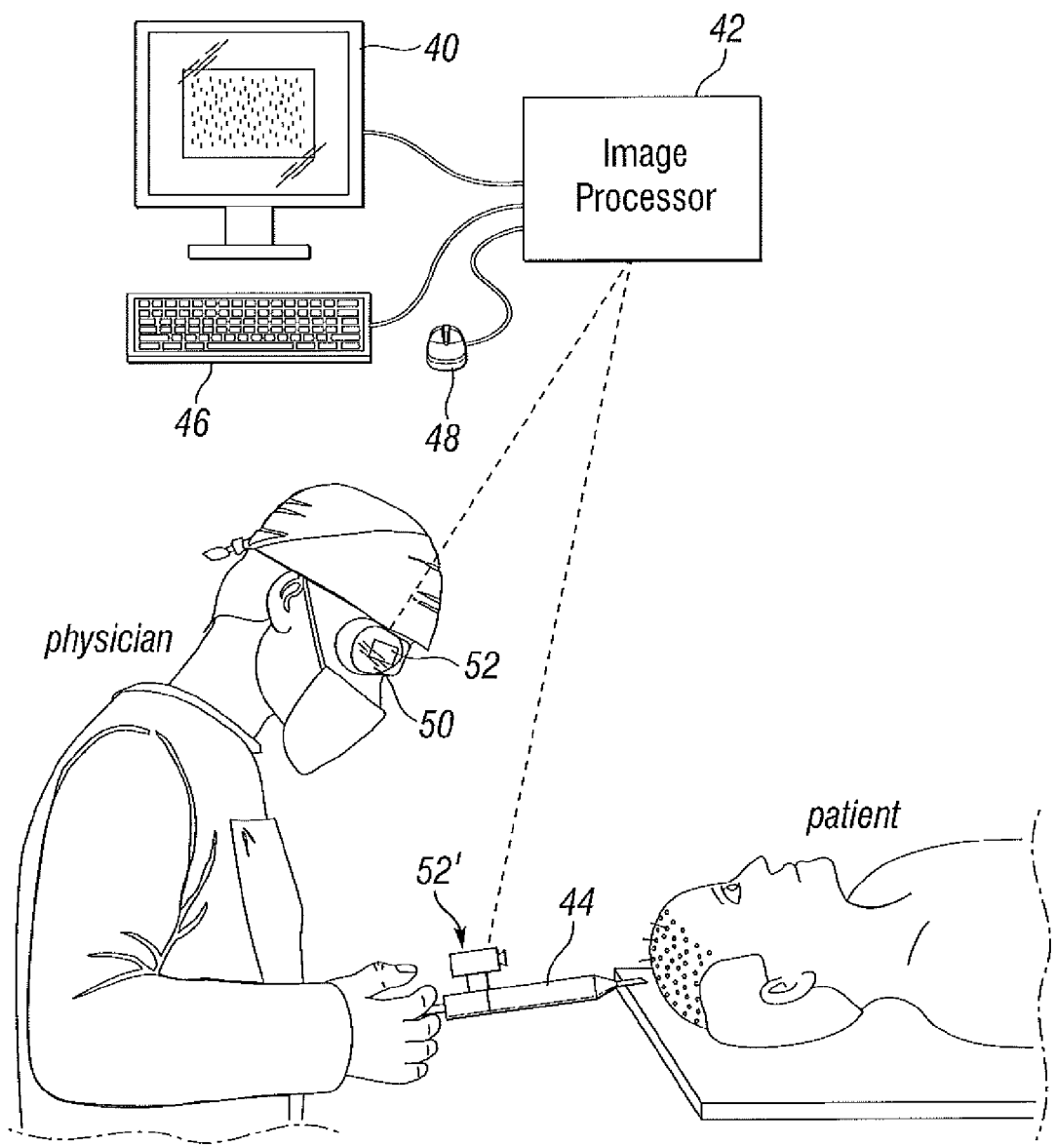
FIG. 10 is a depiction of an exemplary embodiment of the present invention implemented in a non-robotic hair harvesting procedure.

According to another aspect, automatic follicular unit selection may be also implemented in a procedure conducted by the doctor using some hand-held tool for hair harvesting. One such implementation is shown as an example in FIG. 10. In this embodiment, a physician is conducting a manual operation on the patient using a hand-held harvesting tool 44 and wearing the typical glasses 50 that have high-magnification lupes. An image acquisition device 52, such as one or more cameras, may be attached to the glasses. The camera(s) may have viewfinders such that when attached to the glasses it allows the physician to view exactly what the cameras are imaging. Alternatively, the cameras 52' may be attached to the hand-held instrument or tool that physician is using for hair harvesting. In some additional embodiments, it may be a stand-alone image acquisition device. FIG. 10 shows two of the alternative examples of the image acquisition device as 52 (on the glasses) and 52' on the tool 44. The image processor, such as the computer 42, may execute the selection method of the present invention and perform the scene analysis, including highlighting of the follicular units based on the specified policies and/or filters. The monitor 40 displays the highlighted follicular unit or units, as well as other useful data/statistics, for example, an exact count of hair, approximate density, follicular unit types, etc. Guided by the information displayed on the monitor, physician may select the next follicular unit for harvesting.

As will be appreciated by those skilled in the art, the methods of the present invention may be embodied, at least in part, in software and carried out in a computer system or other data processing system. Therefore, in some exemplary embodiments hardware may be used in combination with software instructions to implement the present invention. For example, an article of manufacture of the present invention may comprise a machine-accessible medium including data that, when accessed by a machine, cause the machine to perform operations, such as identifying a pool of candidate follicular units for harvesting in one or more images obtained from an image acquisition device; automatically sorting follicular units in the pool of candidate follicular units based on one or more policies designed to improve one or more of speed, quality and efficacy of the hair harvesting; and automatically selecting a particular follicular unit to be harvested next, wherein a selected follicular unit is one of the best available follicular units based on the at least one or more policies. The article of manufacture may alternatively, or additionally comprise machine-accessible medium including data that, when accessed by a machine, cause the machine to perform operations, such as illuminating with a light source a skin surface having blood on a portion of the skin surface; acquiring an image of the skin surface, including the portion of the skin surface with the blood thereon, while the skin surface is illuminated with the light source; adjusting a wavelength of the light source such that contrast between the image of the skin surface without blood and an image of the blood is minimized; and using the adjusted wavelength of the light source to visualize or improve visualization of a hair graft located in a region of the skin surface having blood thereon.

A machine-readable medium may be used to store software and data which causes the system to perform methods of the present invention. The above-mentioned machine-readable medium may include any suitable medium capable of storing and transmitting information in a form accessible by processing device, for example, a computer. Some examples of the machine-readable medium include, but not limited to, magnetic disc storage, flash memory device, optical storage, random access memory, etc.

The foregoing illustrated and described embodiments of the invention are susceptible to various modifications and alternative forms, and it should be understood that the invention generally, as well as the specific embodiments described herein, are not limited to the particular forms or embodiments disclosed, but to the contrary cover all modifications, equivalents and alternatives falling within the scope of the appended claims. By way of non-limiting example, it will be appreciated by those skilled in the art that particular features or characteristics described in reference to one figure or embodiment may be combined as suitable with features or characteristics described in another figure or embodiment. Applicant regards the subject matter of the invention to include all novel and nonobvious combinations and subcombinations of the various elements, features, functions, and/or properties disclosed herein. No single feature, function, element or property of the disclosed embodiments is essential.

What is claimed is:

1. A method for improving visualization of hair for use in hair transplantation, the method comprising:
    illuminating with a light source a skin surface having blood on a portion of the skin surface;
    acquiring an image of the skin surface, including the portion of the skin surface with the blood thereon, while the skin surface is illuminated with the light source;
    adjusting a wavelength of the light source such that contrast between the image of the skin surface without blood and an image of the blood is minimized; and using the adjusted wavelength of the light source to visualize or improve visualization of a hair graft located in a region of the skin surface having blood thereon.

2. The method of claim 1, wherein adjusting comprises acquiring an image to verify that the contrast between the image of the skin surface without blood and the image of the blood has been minimized.

3. The method of claim 2, wherein if the contrast has not been minimized as desired, repeating the step of adjusting the wavelength of the light source and acquiring one or more additional images to verify, until the contrast between the image of the skin surface without blood and the image of the blood has been minimized as desired.

4. The method of claim 1, wherein adjusting comprises selecting the adjusted wavelength of the light source from a look-up table.

5. The method of claim 1, wherein adjusting comprises selecting the adjusted wavelength of the light source from patient specific information.

6. The method of claim 1, further comprising storing the adjusted wavelength information in a database.

7. The method of claim 1, wherein the region of the skin surface where the hair graft is located is the same or different than the bloody portion of the skin surface referred to in the adjusting step.

8. The method of claim 1, wherein the light source comprises at least two substantially monochromatic emitters, and adjusting the wavelength of the light source comprises adjusting the relative contribution from the at least two emitters.

9. The method of claim 8, wherein one of the at least two emitters has a wavelength in the region of 640-690 nm and another of the at least two emitters has a wavelength in the region of 685 to 790 nm.

10. The method of claim 1, wherein acquiring the image of the skin surface comprises detecting an intensity of reflection of light from the skin surface without blood and detecting an intensity of reflection of light from the blood.

11. The method of claim 1, comprising adjusting a wavelength of the light source such that the contrast between the image of the skin surface without blood and the image of the blood is substantially zero.

12. The method of claim 1, wherein the skin surface is illuminated with red light of the range of 630 nm to 790 nm.

13. The method of claim 1, wherein the light source comprises a light emitting diode (LED).

14. The method of claim 1, further comprising harvesting the hair graft for transplantation.

15. The method of claim 1, wherein the method is at least partially automated.

16. The method of claim 15, wherein partial automation comprises illuminating the skin surface with the light source configured in a first configuration and detecting a first contrast in a first image between the blood and the skin surface without blood, and automatically adjusting the light source to a second configuration to illuminate the skin surface and detecting a second contrast in a second image between the blood and the skin surface without blood.

17. The method of claim 14, further comprising adjusting a wavelength of the light source to enable visualizing a location from which the hair graft has been harvested prior to harvesting a subsequent hair graft.

18. An article of manufacture comprising a machine-accessible medium including data that, when accessed by a machine, cause the machine to perform operations, comprising:
   illuminating with a light source a skin surface having blood on a portion of the skin surface;
   acquiring an image of the skin surface, including the portion of the skin surface with the blood thereon, while the skin surface is illuminated with the light source;
   adjusting a wavelength of the light source such that contrast between the image of the skin surface without blood and an image of the blood is minimized; and
   using the adjusted wavelength of the light source to visualize or improve visualization of a hair graft located in a region of the skin surface having blood thereon.

19. The article of manufacture of claim 18, wherein adjusting comprises selecting the adjusted wavelength of the light source from a look-up table.

20. The article of manufacture of claim 18, wherein illuminating comprises illuminating with a light source comprising at least two emitters.

21. The article of manufacture of claim 20, wherein adjusting the wavelength of the light source comprises adjusting the relative contribution from the at least two emitters.

22. The article of manufacture of claim 20, wherein the machine is further caused to select the contribution value for each of the at least two emitters such that the contrast between the image of the skin surface and the image of the blood is minimized.

23. The article of manufacture of claim 18, wherein the machine accessible medium comprises magnetic disc storage, flash memory device, optical storage, or random access memory.

24. The article of manufacture of claim 20, wherein the machine is caused to perform an operation of cycling the at least two emitters through a number of configurations and processing images acquired from the number of configurations.

25. The method of claim 1, wherein the light source comprises a superluminescent diode (SLED).

* * * * *

UNITED STATES PATENT AND TRADEMARK OFFICE
CERTIFICATE OF CORRECTION

| | | |
|---|---|---|
| PATENT NO. | : 8,652,186 B2 | Page 1 of 1 |
| APPLICATION NO. | : 12/824801 | |
| DATED | : February 18, 2014 | |
| INVENTOR(S) | : Roy et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 631 days.

Signed and Sealed this
Second Day of June, 2015

Michelle K. Lee
*Director of the United States Patent and Trademark Office*